(12) United States Patent
Moon

(10) Patent No.: US 11,969,252 B2
(45) Date of Patent: Apr. 30, 2024

(54) METHOD AND SYSTEM FOR CONTINUOUS MONITORING OF PATIENTS FOR ARRHYTHMIAS

(71) Applicant: TriVirum, Inc., Lincoln, CA (US)

(72) Inventor: Jim Moon, Lincoln, CA (US)

(73) Assignee: TRIVIRUM, INC., Lincoln, CA (US)

( * ) Notice: Subject to any disclaimer, the term of this patent is extended or adjusted under 35 U.S.C. 154(b) by 0 days.

(21) Appl. No.: 18/386,212

(22) Filed: Nov. 1, 2023

(65) Prior Publication Data

US 2024/0057922 A1 Feb. 22, 2024

Related U.S. Application Data

(63) Continuation of application No. 17/529,185, filed on Nov. 17, 2021.

(60) Provisional application No. 63/144,433, filed on Feb. 1, 2021, provisional application No. 63/114,996, filed on Nov. 17, 2020.

(51) Int. Cl.
*A61B 5/333* (2021.01)
*A61B 5/00* (2006.01)
*A61B 5/256* (2021.01)
*A61B 5/257* (2021.01)
*A61B 5/339* (2021.01)
*A61B 5/361* (2021.01)

(52) U.S. Cl.
CPC .............. *A61B 5/333* (2021.01); *A61B 5/256* (2021.01); *A61B 5/257* (2021.01); *A61B 5/339* (2021.01); *A61B 5/361* (2021.01); *A61B 5/6823* (2013.01); *A61B 2562/0219* (2013.01)

(58) Field of Classification Search
None
See application file for complete search history.

(56) References Cited

U.S. PATENT DOCUMENTS 5,732,708 A * 3/1998 Nau .................... A61N 1/3702
600/510
7,447,544 B1 * 11/2008 Kroll .................... A61N 1/025
607/9

OTHER PUBLICATIONS

Gan and Learmonth, Comparing entropy with tests for randomness as a measure of complexity in time series. Accessed online at: https://arxiv.org/ftp/arxiv/papers/1512/1512.00725.pdf, published Dec. 2, 2015, 21 pages.

* cited by examiner

*Primary Examiner* — Kennedy Schaetzle
(74) *Attorney, Agent, or Firm* — Acuity Law Group, PC; Michael A. Whittaker

(57) ABSTRACT

Body-worn systems and methods for continuously monitoring a patient for cardiac electrical signals and identifying rhythm abnormalities including atrial fibrillation.

16 Claims, 5 Drawing Sheets

METHOD AND SYSTEM FOR CONTINUOUS MONITORING OF PATIENTS FOR ARRHYTHMIAS

The present invention is a continuation of U.S. patent application Ser. No. 17/529,185, filed Nov. 17, 2021, which claims the benefit of U.S. Provisional Application No. 63/114,996, filed Nov. 17, 2020, and to U.S. Provisional Application No. 63/144,433, filed Feb. 1, 2021, each of which is hereby incorporated by reference in its entirety and from each of which priority is claimed.

FIELD OF THE INVENTION

The present invention relates to continuous cardiac monitoring of individuals for arrythmias.

BACKGROUND OF THE INVENTION

The following discussion of the background of the invention is merely provided to aid the reader in understanding the invention and is not admitted to describe or constitute prior art to the present invention.

Atrial fibrillation (AF) is a supraventricular tachyarrhythmia with uncoordinated atrial activation and consequently ineffective atrial contraction. Characteristics on an electrocardiogram (ECG) include 1) irregular R-R intervals (when atrioventricular (AV) conduction is present), 2) absence of distinct repeating P waves, and 3) irregular atrial activity. AF may be triggered by potentially reversible, or acute, causes such as surgery (cardiac and noncardiac), hyperthyroidism, myocarditis or pericarditis, myocardial infarction, pulmonary embolism, pneumonia, and alcohol intoxication.

While loop recorders, pacemakers, and defibrillators offer the possibility of reporting frequency, rate, and duration of abnormal atrial rhythms, including AF, a challenge to the use of body-worn AF monitors for continuous monitoring and reporting of AF arises from noise and artifacts prevalent in ambulatory monitors, resulting in false alarms, irrelevant data that is incorrectly identified for analysis, and a resulting alarm fatigue.

SUMMARY OF THE INVENTION

It is an object of the invention to provide body-worn systems and methods for continuously monitoring a patient for cardiac electrical signals and identifying rhythm abnormalities including atrial fibrillation. The systems and methods described herein reduce the amount of storage that is required to make diagnostic decisions regarding the presence or absence of the arrhythmia in question by only storing segments of the patient's electrocardiogram during the onset and the offset of the arrhythmia, thus providing many hours of monitoring capacity in a small and easily worn form factor.

In a first aspect, the present invention relates to a body-worn ECG monitor that captures and records snippets of ECG waveform data that brackets an onset of a change in cardiac rhythm. While described hereinafter in terms of capturing onset or termination of an arrhythmia (e.g., a transition from normal sinus rhythm to atrial fibrillation, or from atrial fibrillation to normal sinus rhythm), the devices and systems described herein are applicable to any abrupt change in cardiac rhythm that may be observed through the use of ECG waveform analysis.

In certain embodiments, the body-worn ECG monitor of the invention comprises:
at least one ECG lead configured be worn on the body of an individual and to measure electrical signals indicative of electrical activity of the individual's cardiac cycle on a continuous basis and generate therefrom an analog waveform;
sensor electronics comprising an analog-to-digital converter operably connected to the at least one ECG lead to receive the analog waveform or a frequency-filtered form thereof and to generate therefrom a digital waveform;
a processing component operably connected to the sensor electronics and configured to receive the digital waveform and to continuously monitor the digital waveform for changes in cardiac rhythm indicative of a transient arrhythmic event by
(i) storing a segment of the digital waveform in a circular data buffer, wherein the stored segment contains digital data for the current cardiac cycle and a plurality of consecutive previous cardiac cycles, and wherein the stored segment is of time length $l_1$ and is continuously updated for new cardiac cycles,
(ii) processing the digital waveform on a beat-by-beat basis to identify an occurrence of a first rhythm transition from a normal cardiac rhythm to an arrhythmia,
(iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;
(iv) following the first rhythm transition, processing the digital waveform on a beat-by-beat basis to identify an occurrence of a second rhythm transition from the arrhythmia to a normal cardiac rhythm;
(v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and
(vi) repeating steps (ii)-(vi).

The time lengths $l_2$, $l_3$, $l_4$, and $l_5$ are preferably selected to capture a desired number of cardiac cycles before and after the event trigger (an identified change in rhythm). For example, in an individual with a normal sinus pulse rate of 60 bpm, 10 seconds would be expected to capture 10 normal cardiac cycles. In certain embodiments, $l_2$ and $l_4$ can be the same time length, and the time lengths time lengths $l_3$ and $l_5$ can be the same time length.

In preferred embodiments, time lengths $l_2$ and $l_3$ are selected to provide at least about 10 seconds of recorded data that includes the first rhythm transition; or between about 10 and about 240 seconds of recorded data that includes the first rhythm transition; or between about 60 and about 120 seconds of recorded data that includes the first rhythm transition. Similarly, time lengths $l_4$ and $l_5$ are selected to provide at least about 10 seconds of recorded data that includes the second rhythm transition; or between about 10 and about 240 seconds of recorded data that includes the second rhythm transition; or between about 60 and about 120 seconds of recorded data that includes the second rhythm transition.

In certain embodiments, the circular data buffer holds at least a portion of the digital waveform equal to $l_2$ or $l_4$, whichever is greater in order to provide a look-back into the previous cardiac cycles sufficient for recording of the desired data snippet. For example, if a first rhythm transition occurs at time t, and $l_2$ seeks to recover data from the circular data buffer beginning from a point in the data preceding the first rhythm transition by a predetermined time length $l_2$, then $l_1$ (the size of the buffer) must equal or greater than $l_2$ in order to obtain the necessary data.

In certain embodiments, the first and second rhythm transitions are identified by calculating a randomness score for a series of R-R intervals from the digital waveform using the processing component. Examples of such randomness scores include an entropy values calculated using methods known in the art as Approximate Entropy (ApEn), Sample Entropy (SampEn), Permutation Entropy (PermEn), and Multi-Scale Entropy (MSE). This list is not meant to be limiting. Preferably the randomness score (e.g., entropy value) is calculated for at least about 32, more preferably at least about 64, even more preferably about 128, and still more preferably about 256 or more consecutive QRS complexes in the digital waveform.

In certain embodiments, the body-worn ECG monitor according to the invention is further configured to communicate with an external device to download data stored in the storage memory (e.g., a flash memory) to a storage medium on the external device. The connection between the storage memory in the ECG monitor and the external device may be a direct wired (e.g., WiFi, USB, Ethernet, Firewire, I2C, RS422, CAN, etc.) or wireless (e.g., Bluetooth, Zigbee, ANT+, infrared, etc.) data connection managed by the processing component of the ECG monitor (e.g., a microprocessor or microcontroller). Alternatively, reading the storage memory of the ECG monitor may be managed by the external device through an adapter connected between the storage memory itself and a compatible port on the external device.

In certain embodiments, the body-worn ECG monitor according to the invention may be connected to electrodes that provide the at least one ECG lead by external cabling or wirelessly by means of a transceiver operably connected to the electrodes which communicates with the sensor electronics and the processing component worn separately from the electrodes. In preferred embodiments, the electrodes that provide the at least one ECG lead are provided in the form of an integral or unitary device which further comprises the sensor electronics and the processing component.

By way of example, a single lead ECG monitor according to the invention may comprise a pair of electrodes on the underside of a flexible body coupled to a housing as an integral or unitary device. Two electrode traces in the flexible body connect to the sensor electronics, which is in turn connected to the processing component. The ECG monitor is then affixed to the individual being monitored by means of an adhesive on the flexible body on the chest at about the level of the heart such that one of the electrodes is positioned superior relative to the other. This provides a "modified lead II" configuration that is adequate for determining rhythm and for observing the presence or absence of p-waves. Thus, in a related aspect, the present invention relates to such an integral or unitary single lead ECG monitor.

In certain embodiments, the single lead ECG monitor of the present invention comprises an accelerometer within the housing that is coupled to the processing component such that the processing component can determine an orientation of the two electrodes and thereby determine which electrode is superior to the other on the body. In this way, the "up/down" orientation of the monitor is not critical when being affixed to the individual. This can provide improved ease of use, particularly in an environment where the single lead ECG monitor is intended to be affixed by the wearer themselves rather than by a medical practitioner, as there is no "wrong" orientation. Rather, the device itself understands the orientation of the single lead ECG monitor on the body from the accelerometer signals and adapts the ECG waveforms accordingly for processing.

In certain other embodiments, the orientation of the monitor is determined by the polarity of the signal received from the modified lead II electrodes. In this configuration, the normal polarity of negative at the upper electrode and positive at the lower electrode. The processing component can read the waveform and "flip" the sign of the waveform as required to obtain the correct polarity. Again, the "up/down" orientation of the monitor is not critical when being affixed to the individual.

In a related aspect, the present invention relates to a system, comprising,
  the body-worn ECG monitor according to the present invention; and
  the external device, wherein the external device comprises a microprocessor and a non-volatile memory operably connected to the microprocessor, wherein the microprocessor is configured to execute code stored on the non-volatile memory or downloaded from a network location, wherein executing the code causes the external device to display the data downloaded to the storage medium as graphical depictions of ECG waveform segments.

The external device may be any computing device capable of receiving data from the ECG monitor and displaying the data. By way of example, a tablet, personal computer, smartphone, etc., running the necessary computer code is capable of displaying graphical depictions of ECG waveform segments either on screen or in printed form.

In yet another related aspect, the present invention comprises a method of continuously monitoring a patient for cardiac electrical signals and identifying rhythm abnormalities. These methods comprise affixing the body worn monitor to the individual, the affixing comprising placing two or more electrodes on the individual that provide the at least one ECG lead, and causing the processing component operably connected to the sensor electronics to receive the digital waveform from the at least one ECG lead and to continuously monitor the digital waveform for changes in cardiac rhythm indicative of a transient arrhythmic event as described above.

It is another object of the invention to provide body-worn systems and methods for continuously monitoring a patient for cardiac electrical signals. Because of the directional dependency of voltage-based assessment of myocardium (referred to as "polarity"), an orientation agnostic voltage assessment would allow for a consistent physiological description of the myocardium being interrogated. Thus, the systems and methods described herein provide improved ease of use by being unaffected by the orientation of the cardiac monitor relative to the patient. Such a device is said to be "orientation agnostic"

In a first aspect of this object, the present invention provides a single lead ECG monitor, comprising
  a pair of electrodes on the underside of a flexible body coupled to a housing as an integral or unitary device;

electrode traces in the flexible body operably connected the pair of electrodes and to sensor electronics comprising an analog-to-digital converter to receive an analog waveform from the pair of electrodes, or a frequency-filtered form thereof, and to generate therefrom a digital ECG waveform; and a processing component operably connected to the sensor electronics within the housing and configured to receive the digital ECG waveform;

wherein the single lead ECG monitor is configured to be affixed to an individual on the chest at about the level of the heart such that one of the electrodes is positioned superior relative to the other on the individual such that the digital ECG waveform approximates a lead II configuration on the individual, wherein the processing component is configured to process the digital ECG waveform and determine therefrom an orientation of the electrodes on the individual such that the single lead ECG monitor is agnostic to the polarity of the digital ECG waveform, and wherein the processing component is further configured to produce ECG data having standard lead II polarity based on the orientation of the electrodes determined by the processing component.

In certain embodiments, the orientation of the electrodes on the individual is determined by causing the processing component to initially assign an orientation of the electrodes. That is, one of the electrodes is assumed to be the negative electrode and thus considered to be in a superior position to relative to a second electrode of the pair of electrodes for purposes of producing the ECG data. From the ECG waveform collected under this assumed orientation, the processing component determines a polarity metric. If the polarity metric indicates that the initial orientation assigned to the electrodes was incorrect, the processing component reassigns the electrode pair; that is, the second electrode of the pair of electrodes becomes the negative (superior) electrode for purposes of producing ECG data from the waveform. Conversely, if the polarity metric indicates that the initial orientation assigned to the electrodes was correct, the first electrode of the pair of electrodes remains the negative (superior) electrode for purposes of producing ECG data from the waveform A variety of polarity metrics may be used, either individually or in combination, for the orientation determination. For example, the polarity may be determined from one or more of (a) a slope of the leading edge of the QRS complex, (b) an amplitude of the largest positive wave, (c) an amplitude of the deepest negative wave, (d) a polarity of the R wave, (e) a polarity of the T-wave, and (f) a polarity of the P-wave. This list is not meant to be limiting. In various embodiments, the polarity metric can comprise one or more of the following determinations:

if the initial slope of the QRS leading edge is negative and the T-wave is negative, then the polarity metric indicates that the initial orientation assigned to the electrodes was incorrect, if the initial slope of the QRS leading edge is negative and the P-wave is negative, then the polarity metric indicates that the initial orientation assigned to the electrodes was incorrect, if the T-wave is negative and the P-wave is negative, then the polarity metric indicates that the initial orientation assigned to the electrodes was incorrect; or if the amplitude of the largest negative wave is larger than the amplitude of the largest positive wave, then the polarity metric indicates that the initial orientation assigned to the electrodes was incorrect.

The choice of polarity metric may be encoded in a storage memory of the processing component, and may be dependent upon the electrical activity of the individual being monitored. For example, primary T-wave inversions are associated with benign syndromes, such as the persistent juvenile T-wave pattern and the digitalis effect, as well as morbid conditions, including acute coronary ischemic events, pulmonary embolism, myocarditis, etc. Secondary T-wave changes result from aberrant ventricular activation in the context of normal action potential characteristics; examples include bundle-branch blocks, ventricular pre-excitation states (eg, Wolff-Parkinson-White syndrome), ventricular paced rhythms, and ventricular ectopic beats. Altered P wave morphology may be seen in left or right atrial enlargement. The medical practitioner may consider the cardiac electrical activity of each individual patient in determining a suitable polarity metric.

Because noise and artifacts are inherent contaminating components and are particularly present in ambulatory ECG monitoring, in certain embodiments the polarity metric is determined from data in the digital ECG waveform representing a plurality of consecutive cardiac cycles. For example, the polarity metric is determined from data in the digital ECG waveform representing at least 2, 5, 10, 20, 50, or more consecutive cardiac cycles. In these embodiments, the processing component of the single lead ECG monitor only assigns an orientation if at least 70%, 75%, 80%, 85%, 90%, 95% or more of the selected number of consecutive cardiac cycles agree on the orientation of the electrodes before the polarity metric is used to produce the ECG data.

By way of example, if 10 consecutive cardiac cycles are used to determine the polarity metric, and at least 80% must agree on orientation, if the percentage is not met the monitor can restart the determination with the next 10 consecutive cardiac cycles, and continue until the 80% threshold is met or the system reaches a time-out condition that instructs the single lead ECG monitor to halt and signal an error condition. If an error condition is signaled, the individual can be instructed to remove and reattach the single lead ECG monitor, obtain a replacement, or contact a health care provider for instructions.

Because the single lead ECG monitor is recording an electrical signal from the individual, the monitor can determine if the single lead ECG monitor has been dislodged from the individual based on a loss of signal. This dislodgement may be accidental or when the individual temporarily removes the device. In certain embodiments, the orientation of the electrodes is may be redetermined by the processing component when the processing component determines from the digital ECG waveform that at least one of the pair of electrodes has been lost, but has now been repositioned on the individual. In other embodiments, the orientation of the electrodes may be redetermined at a predetermined interval during continued use of the ECG data system to confirm that the single lead ECG monitor has remained in its previous orientation.

In certain embodiments, following determination of the orientation of the electrodes by the processing component, the single lead ECG monitor continuously monitors the digital ECG waveform, and in preferred embodiments the single lead ECG monitor monitors the individual for changes in cardiac rhythm indicative of a transient arrhythmic event such as atrial fibrillation. By way of example, the processing component can provide a warning, either on the single lead ECG monitor itself or on a remote device. The warning could be from a sound, a blinking light or a vibration of the single lead ECG monitor. The aspect of the device would allow the user to know he/she has an abnormal waveform and contact the health care professional. Alternatively, the single lead ECG monitor can wirelessly signal a remote monitoring station directly without action by the individual.

In certain embodiments, the single lead ECG monitor according to the invention is further configured to communicate with an external device to download data stored in the storage memory (e.g., a flash memory) to a storage medium on the external device. The connection between the storage memory in the ECG monitor and the external device may be a direct wired (e.g., WiFi, USB, Ethernet, Firewire, I2C, RS422, CAN, etc.) or wireless (e.g., Bluetooth, Zigbee, ANT+, infrared, etc.) data connection managed by the processing component of the single lead ECG monitor (e.g., a microprocessor or microcontroller). Alternatively, reading the storage memory of the single lead ECG monitor may be managed by the external device through an adapter connected between the storage memory itself and a compatible port on the external device.

In certain embodiments, the external device further comprises a non-volatile memory operably connected to the microprocessor, wherein the microprocessor is configured to execute code stored on the non-volatile memory, wherein executing the code causes the external device to display the data downloaded to the storage medium as graphical depictions of ECG data; and executing the code on the microprocessor to display the ECG data.

In certain embodiments, the single lead ECG monitor according to the invention may be connected to electrodes that provide the at least one ECG lead by external cabling or wirelessly by means of a transceiver operably connected to the electrodes which communicates with the sensor electronics and the processing component worn separately from the electrodes. In preferred embodiments, the electrodes that provide the at least one ECG lead are provided in the form of an integral or unitary device which further comprises the sensor electronics and the processing component.

By way of example single lead ECG monitor according to the invention may comprise a pair of electrodes on the underside of a flexible body coupled to a housing as an integral or unitary device. Two electrode traces in the flexible body connect to the sensor electronics, which is in turn connected to the processing component. The ECG monitor is then affixed to the individual being monitored, e.g., by means of an adhesive on the flexible body, on the chest at about the level of the heart such that one of the electrodes is positioned superior relative to the other. This provides the "modified lead II" configuration that is adequate for determining rhythm and for observing the presence or absence of p-waves. Thus, in a related aspect, the present invention relates to such an integral or unitary single lead ECG monitor.

In preferred embodiments, the single lead ECG monitor captures and records snippets of ECG waveform data that brackets an onset of a change in cardiac rhythm. While described hereinafter in terms of capturing onset or termination of an arrhythmia (e.g., a transition from normal sinus rhythm to atrial fibrillation, or from atrial fibrillation to normal sinus rhythm), the devices and systems described herein are applicable to any abrupt change in cardiac rhythm that may be observed through the use of ECG waveform analysis. by (i) storing a segment of the digital ECG waveform in a circular data buffer, wherein the stored segment contains digital data for the current cardiac cycle and a plurality of consecutive previous cardiac cycles, and wherein the stored segment is of time length $h_i$ and is continuously updated for new cardiac cycles, (ii) processing the digital ECG waveform using the processing component on a beat-by-beat basis to identify an occurrence of a first rhythm transition from a normal cardiac rhythm to an arrhythmia, (iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;

(iv) following the first rhythm transition, processing the digital ECG waveform using the processing component on a beat-by-beat basis to identify an occurrence of a second rhythm transition from the arrhythmia to a normal cardiac rhythm;

(v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and (vi) repeating steps (ii)-(vi).

The single lead ECG monitor of the invention can be affixed to the individual to be monitored using a variety of attachment mechanisms as described hereinafter. In certain embodiments the single lead ECG monitor is configured to attach to the individual by means of an adhesive on the flexible body of the single lead ECG monitor.

In related embodiments, the present invention provides methods for monitoring a cardiac electrical activity in an individual, comprising:

affixing a single lead ECG monitor according to the invention to the patient;

receiving a digital ECG waveform at the processing component;

executing code on the processing component to determine an orientation of the electrodes on the individual; and recording ECG data having standard lead II polarity for a period of time based on the orientation of the electrodes determined by the processing component from the digital waveform, wherein the ECG data is stored in a storage memory of the single lead ECG monitor.

The stored ECG data may be the raw waveform data, or may be a processed form thereof, and may be continuous data or may be discontinuous data snippets.

In certain embodiments, the ECG data in the storage memory of the single lead ECG monitor may be accessed by an external device. By way of example, the method further comprises operably connecting the ECG monitor to an external device comprising a microprocessor and a storage medium; and downloading the recorded ECG data to the storage medium.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

ECG

At every heartbeat, the heart is depolarized to trigger its contraction. From the sinoatrial node (SAN), the wave of depolarization spreads across the atria to the atrioventricular node (AVN). The impulse is delayed briefly at the AVN and atrial contraction is completed. The wave of depolarization then proceeds rapidly to the bundle of His where it splits into two pathways and travels along the right and left bundle branches. The impulse travels the length of the bundles along the interventricular septum to the base of the heart, where the bundles divide into the Purkinje system. From here, the wave of depolarization is distributed to the ventricular walls and initiates ventricular contraction.

The ECG is a recording of the heart's electrical activity during this "cardiac cycle". The electrical signals indicative of the cardiac cycle may be sensed as changes in electrical potential between two measurement points on the body. Depending on the number of electrodes and their position on the body, multiple views of the heart's electrical activity can be recorded. An ECG "lead" is a measure of differences in potential measured between two points. A simple lead is composed of two electrodes; a negative (reference) electrode and a positive (exploring) electrode.

A standard 12-lead ECG uses 10 electrodes to obtain 12 electrical measurements of the heart. Three bipolar leads and three unipolar leads are obtained from three electrodes attached to the left arm, the right arm, and the left leg, respectively. An electrode is also attached to the right leg as a ground electrode. These electrodes provide the following leads:

lead I: right arm-left arm
lead II: right arm-left leg
lead III: left leg-left arm The unipolar leads reflect the potential difference between one of the three limb electrodes and an estimate of zero potential—derived from the remaining two limb electrodes. These leads are known as augmented leads. The augmented leads and their respective limb electrodes are:

aVR lead: right arm
aVL lead: left arm
aVF lead: left leg

Another six electrodes, placed in standard positions on the chest wall, give rise to six unipolar (precordial) leads V1-V6.

Figure 4:
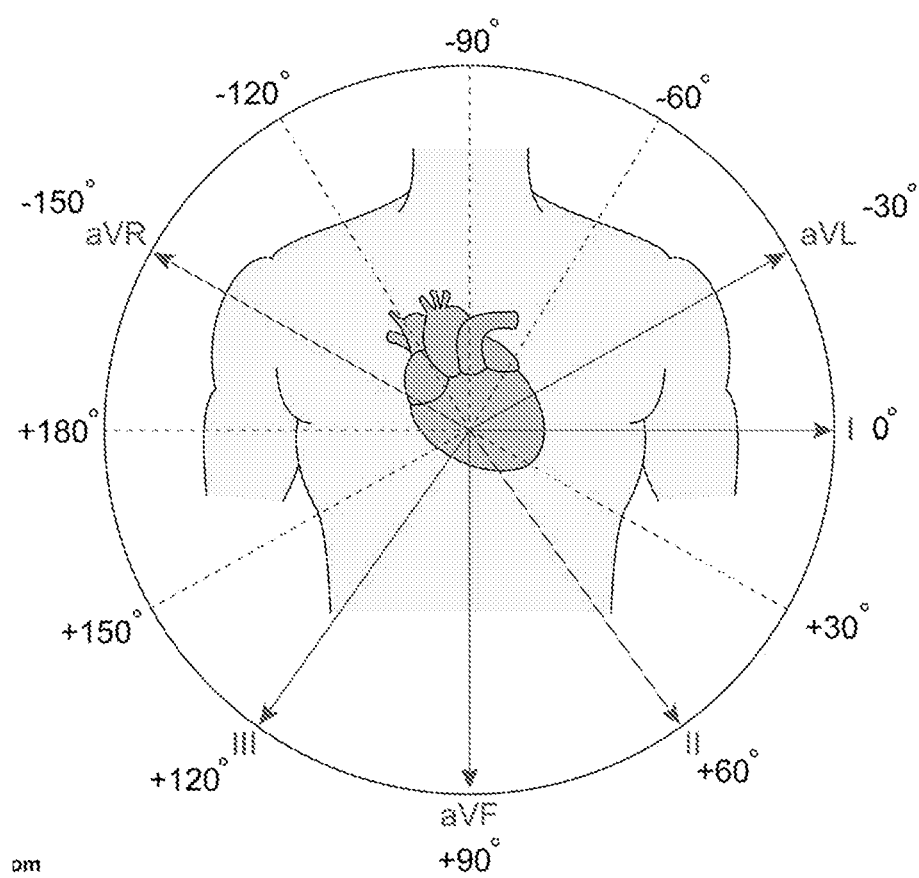
FIG. 4 depicts a conventional axial reference system for ECG monitor of the invention showing augmented leads $aV_L$, $aV_R$, and $aV_F$.

Lead II, for example, records the electrical activity as seen from the inferior (diaphragmatic) surface of the heart along a plane that is approximately vertical through the heart. See, FIG. 4. For lead II, the reference electrode is superior to the exploring electrode. A "modified" lead II may be provided by positioning a pair of electrodes on the chest at about the level of the heart, with one electrode being positioned superior to the other.

In the devices described herein, it can be advantageous to use this modified lead II orientation of the electrodes as a single lead system, as this is both simple and provides the necessary data to assess an arrhythmia such as atrial fibrillation. For ECG lead II, a wave a depolarization traveling toward the exploring electrode produces a positive deflection in the lead, and a maximal positive deflection is recorded in lead II when the depolarization wave travels parallel to sampled the axis.

By providing an accelerometer in the device, it is unnecessary to predefine which of the two electrodes is the reference (superior) electrode. Rather, the device can be placed on the monitored individual with either electrode in the superior position, and the device itself can determine the orientation of the electrodes and thus correctly measure the potential difference between these electrodes. Alternatively, the device can determine the polarity of the incoming lead waveform and invert the sign of the signal so that whichever electrode in the lead is supposed to be the positive lead is read as positive.

R-R Interval Measurement

The R-R interval measurement begins with the identification of a QRS complex distinct from any noise or artifact that may be present, and the further identification of a consistent fiducial point within the QRS complex. Upon identification of a QRS complex and the corresponding fiducial point, the associated R-R interval is the time between the newly determined fiducial point and a corresponding fiducial point in the previous QRS complex. Because the sample rate of the ECG waveform determines the resolution of the R-R interval, it must be fast enough to provide adequate differentiation in the subsequent randomness calculation of the R-R intervals to distinguish atrial fibrillation from non-atrial fibrillation rhythms. The determination of the fiducial point of the QRS complex begins with the determination and removal of the noise elements of the signal. This is accomplished with a band-pass (e.g., 5 to 50 Hz) filter followed by a series of signal processing steps that determine the time varying signal energy in the in-band signal, where the in-band signal energy is defined as:

$$E_s(n - y/2) = \sum_{i=(n-y)}^{n} |x(n)|^2$$

Where Y is the number of samples within the window and $E_s(n-y/2)$ is the energy at n-y/2. The energy peaks that also meet criteria for polarity and duration are selected as the QRS complex, with the point of peak energy chosen as the fiducial point that marks the time of the R-wave. The time of the newly detected R-wave minus the time of the previous R-wave detection is the R-R interval that is passed to the atrial fibrillation detection algorithm.

Hardware

Figure 2:
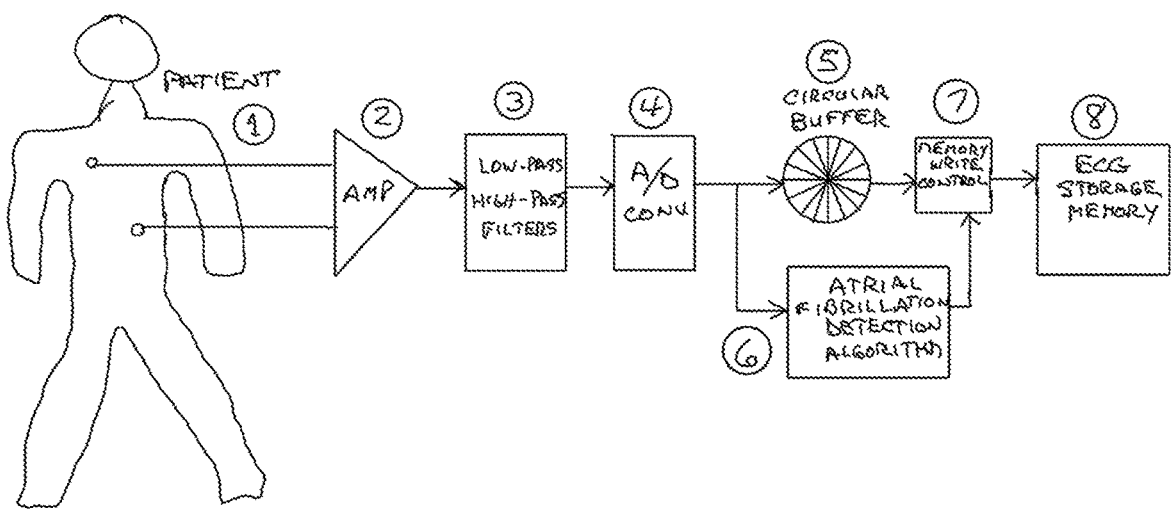
FIG. 2 depicts the general strategy for an exemplary ECG monitor of the present invention in additional detail.

FIG. 2 depicts the general strategy for an exemplary ECG monitor of the present invention. An electrocardiogram is acquired from a patient (1) by means of electrodes attached to the patient. The signal from the electrodes is amplified (2) and filtered (3) to achieve the desired signal bandwidth. The filtered electrocardiogram is converted to a digital data stream by an analog-to-digital converter (4) and stored in a circular data buffer (5). The number of storage locations in the circular buffer is sufficient to store a history of the electrocardiogram for a duration that provides sufficient information to clear observe the patient's cardiac rhythm for a period of time prior to the onset of atrial fibrillation or other arrhythmia to confirm that the cardiac rhythm preceding the arrhythmia of interest (e.g. atrial fibrillation) was in fact not the arrhythmia being detected. An arrhythmia detection algorithm (6) evaluates the cardiac rhythm in real time and, upon detection, provides a control signal to the memory write control element (7) to begin storing the historical electrocardiogram into the electrocardiogram storage memory (8). Similarly, the arrhythmia detection algorithm (6) evaluates the electrocardiogram in real time to detect the cessation of the arrhythmia of interest and signals the memory write control element (7) to record the end of the arrhythmia event with sufficient historical data prior the end of the arrhythmia event to confirm the arrhythmia of interest and to record the transition to a cardiac rhythm that is different from the arrhythmia of interest with sufficient recording time to confirm that the new cardiac rhythm is in fact different from the arrhythmia of interest.

The ECG monitor may be affixed and/or adhered to the body of the individual in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. The monitor may comprise an adhesiveness embodiment (e.g. chest strap), and/or a low-irritation adhesive for sensitive skin, such as hydrocolloid. The ECG monitor may comprise a layer of breathable tape or fabric for adherence to the wearer, for example a gauze, latex, wrap knit, or other types of stretchable and wear-safe material, such as a Tricot-type linen or tricot-knit polyester fabric, to allow moisture vapor and air to circulate to and from the skin of the patient through the tape. The breathable tape can comprise a backing material that provides an adhesive layer. The backing may be conformable and/or flexible, such that the device does not become detached with body movement.

Atrial fibrillation rhythm identification:

Atrial fibrillation is identified by the random nature of R-R intervals that are characteristic of atrial fibrillation. While several arrhythmias exhibit multiple R-R intervals (e.g. bigeminy or trigemini), they are not random, but repeating patterns. To recognize atrial fibrillation from these other arrhythmias, it is necessary to calculate the true random nature of the R-R intervals over a number of consecutive R-R intervals. Approximate Entropy (ApEn) is a statistical measure of the level of randomness of a data series which is based on counting patterns and their repetitions. Low levels of this statistic indicate the existence of many repeated patterns, and high values indicate randomness and unpredictability. Even though ApEn was originally developed after the entropy concept of Information Theory for physiological research, it has been used in different fields from psychology to finance. Alternatives to ApEn include Sample Entropy (SampEn), Permutation Entropy (PermEn), and Multi-Scale Entropy (MSE). See, e.g., arxiv.org/ftp/arxiv/papers/1512/1512.00725.pdf, which is hereby incorporated by reference.

In certain embodiments, the randomness of 128 consecutive R-R intervals is calculated, updating the computation every time a new R-R interval is measured in a rolling manner, with the oldest R-R interval being removed from the list of R-R intervals every time a new R-R interval is added. The output of the randomness computation is a relative measure of randomness where a value of zero corresponds to a set of R-R intervals that are not random, while an output value of 1 indicates that every R-R interval is truly random, and bears absolutely no relationship between any of the other R-R intervals being evaluated.

The response time of the R-R randomness computation can provide the ability to recognize atrial fibrillation in a time sufficiently short to allow for the capture of the ECG waveform starting a number of seconds prior to the transition from a non-atrial fibrillation rhythm to atrial fibrillation such that the transition is captured in a time-limited snippet of the ECG waveform. The calculation of a randomness score is based on concepts developed by Claude Shannon in 1948: given a discrete random variable X, with possible outcomes $x_1, \ldots, x_n$, which occur with probability $P(x_1), \ldots, P(x_n)$, the entropy of X is formally defined as:

$$H(X) = -\sum_{i=1}^{n} P(x_i) \log P(x_i)$$

where the values of xi are the R-R intervals over a range from 1 to n values. The calculations are updated with every new R-R interval such that when the randomness index rises above a threshold, it corresponds to the onset of atrial fibrillation. Similarly, when the randomness index drops below the threshold, it corresponds to the transition from atrial fibrillation to a non-atrial fibrillation rhythm. The value of the index used as the threshold in a preferred embodiment of the invention is 0.72, determined empirically through performance evaluation against industry recognized databases of ECG recordings from patients with atrial fibrillation.

Figure 3:
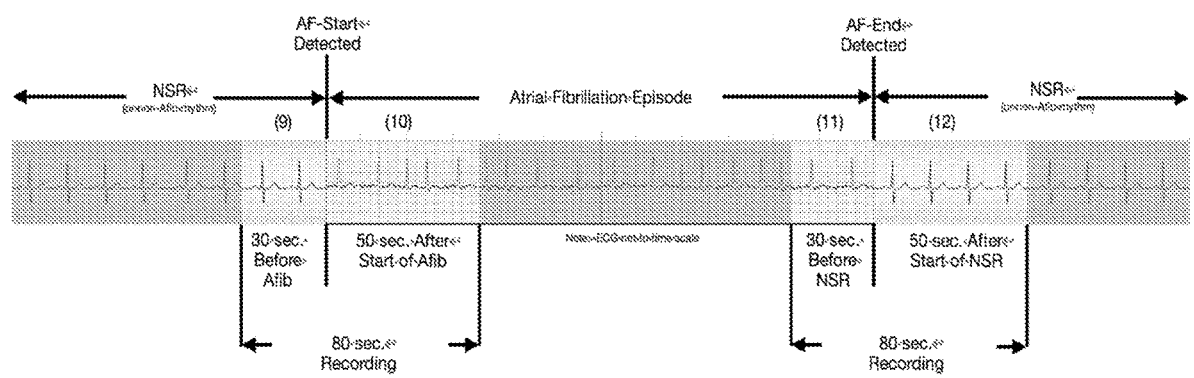
FIG. 3 depicts an exemplary ECG recording scheme for the ECG monitor.

FIG. 3 depicts an exemplary ECG recording scheme for the ECG monitor. The device continuously records data in the circular buffer which stores a limited amount of recent historical ECG data. Initially the subject is in normal sinus rhythm (NSR). Upon detection of the onset of atrial fibrillation (AF-start), a snippet of data is captured from a point 30 seconds before AF-start (obtained from the circular buffer) and terminating 50 seconds after AF-start. When NSR is restored (AF-end), a similar snippet is captured. Each snippet records the transition in rhythm to or from AF and is stored in the storage memory for later review and/or analysis.

Sensor Electronics

Figure 1:
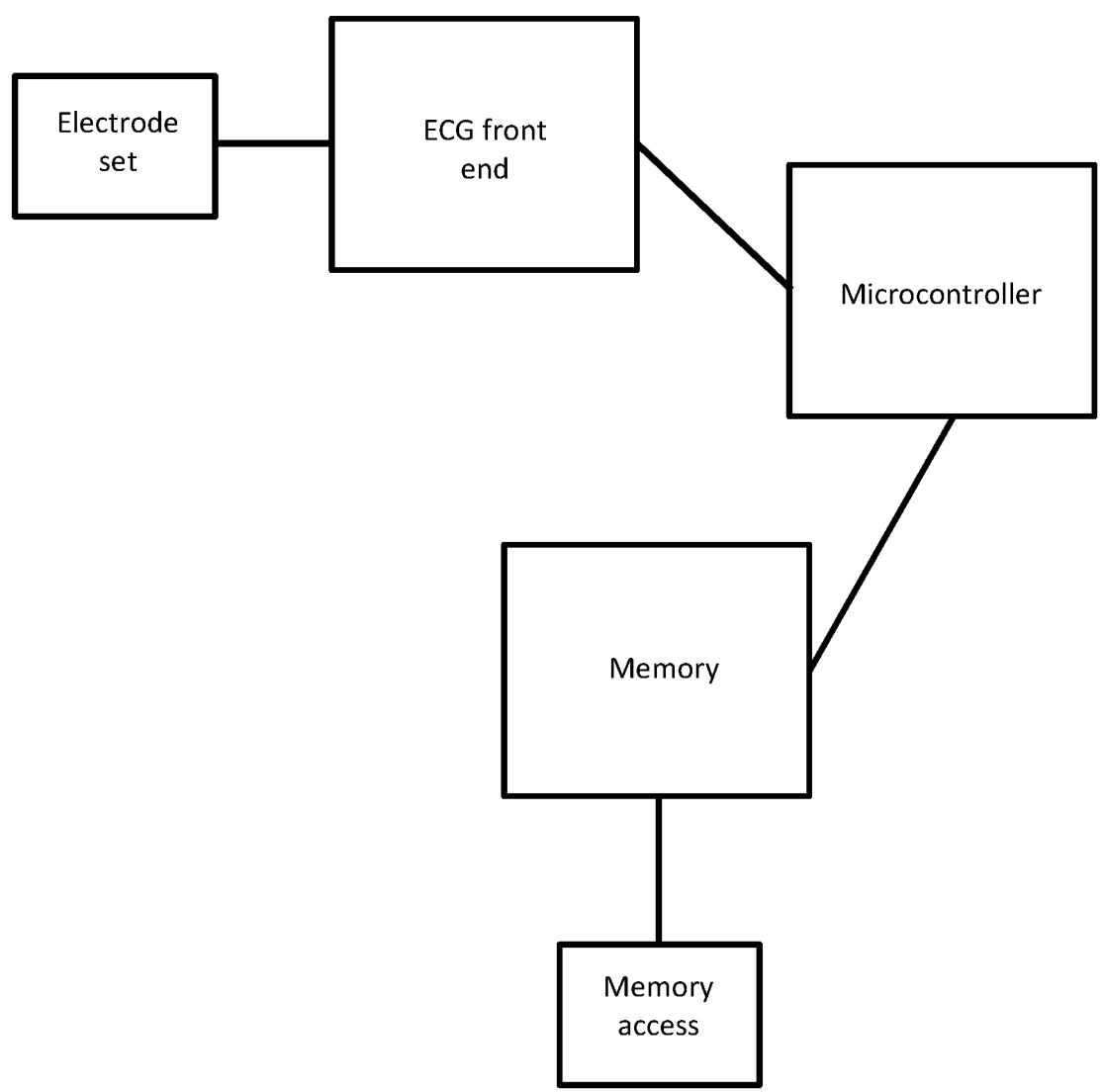
FIG. 1 depicts an exemplary hardware implementation for use in the present invention in schematic form.

FIG. 1 depicts an exemplary hardware implementation for use in the present invention. A number of integrated ECG monitoring circuits are available in the art to provide an interface to ECG electrodes for receiving analog input, signal conditioning, analog-to-digital conversion, etc.

For example, AD8233 (Analog Devices) provides a suitable ECG front end for the ECG monitors described herein. The AD8233 implements a two-pole, high-pass filter for eliminating motion artifacts and the electrode half cell potential. This filter is tightly coupled with the instrumentation amplifier architecture to allow both large gain and high-pass filtering in a single stage, thereby saving space and cost. An uncommitted operational amplifier enables the AD8233 to create a three-pole, low-pass filter to remove additional noise. The user can select the frequency cutoff of all filters to suit different types of applications. To improve the common-mode rejection of the line frequencies in the system and other undesired interferences, the AD8233 includes a right leg drive (RLD) amplifier for driven electrode applications. The AD8233 includes a fast restore function that reduces the duration of the otherwise long settling tails of the high-pass filters. After an abrupt signal change that rails the amplifier (such as a leads off condition), the AD8233 automatically adjusts to a higher filter cutoff. This feature allows the AD8233 to recover quickly, and therefore, to take valid measurements soon after connecting the electrodes to the subject.

Similarly, HM301D (ST Microelectronics) is an integrated front end circuit for ECG devices. A fully integrated analog high pass filter removes the DC component of the signal. Each channel input channel provides high resolution and low noise conversion of biopotential signals up to 10 kHz. A digital filtering and preprocessing (DFP) block implements configurable band-pass filters, IQ impedance demodulation and enable specific algorithm implementation for lead-off check and pacemaker detection. An SPI interface allows the exchange of data with both the microcontroller and other HM301D devices in case of chain connection.

Likewise, MAX30003 (Maxim Integrated) is a complete, biopotential, analog front-end solution for wearable ECG applications. It offers high performance for clinical and fitness applications, with ultra-low power for long battery life. The biopotential channel has ESD protection, EMI filtering, internal lead biasing, DC leads-off detection, ultra-low power leads-on detection during standby mode, and extensive calibration voltages for built-in self-test. Soft power-up sequencing ensures no large transients are injected into the electrodes. The biopotential channel also has high input impedance, low noise, high CMRR, programmable gain, various low-pass and high-pass filter options, and a high-resolution analog-to-digital converter. The biopotential channel is DC coupled, can handle large electrode voltage offsets, and has a fast recovery mode to quickly recover from overdrive conditions, such as defibrillation and electrosurgery.

The processing component comprises a microprocessor or microcontroller, a memory for storage of data processing instructions, implementation of a circular buffer data structure, and to a storage memory for holding data snippets for later retrieval.

An example of a suitable microcontroller is MAX32660 (Maxim Integrated), a 32-bit microcontroller designed for battery-powered devices and wireless sensors. It provides an Arm® Cortex®-M4 processor with floating point unit (FPU); supports SPI, UART, and I²C communication; and includes up to 256 KB of flash memory and 96 KB of RAM to accommodate application and sensor code.

Similarly, STM32L4 (ST Microelectronics) utilizes the ARM® Cortex®-M4 32-bit core operating at a frequency of up to 80 MHz and featuring a FPU, a full set of DSP instructions and a memory protection unit (MPU) which enhances application security. It offers up to 2 Mbyte of Flash (dual bank) and up to 640 Kbytes of SRAM. The entire system performance is optimized using a multi-AHB bus matrix and DMA controllers. It supports I²C communication A circular buffer is a data structure that uses a fixed-size buffer as if it were connected end-to-end. Circular buffering makes a good implementation strategy for a queue that has fixed maximum size. Should a maximum size be adopted for a queue, then a circular buffer is a completely ideal implementation; all queue operations are constant time. A circular buffer can be implemented using four pointers, or two pointers and two integers:

buffer start in memory,
    buffer end in memory, or buffer capacity,
    start of valid data (index or pointer),
    end of valid data (index or pointer), or amount of data
       currently in the buffer (integer);

Preferably, the circular buffer is implemented for direct memory access (DMA). In embedded microcontroller systems, it is common to have a single core CPU. To avoid occupying CPU, most advanced microcontrollers have a Direct Memory Access (DMA) controller. As its name says—DMA does data transfers between memory locations without the need of CPU.

If necessary, a separate Flash memory can also be provided to increase storage capacity of the ECG monitor. By way of example, MT25QU256ABA (Micron Technology) is a 256 Mb, 1.8V Multiple I/O Serial Flash Memory providing It a high-speed SPI-compatible bus interface, execute-in-place (XIP) functionality, advanced write protection mechanisms, and extended address access.

Reading of Data on External Device

When a desired monitoring period has ended, such as about 14 to 21 days in some cases, a patient (or physician, nurse or the like) may remove the ECG monitor, place it in a (prepaid) mailing pouch, and the device to a data processing facility. At this facility, the stored data snippets may be downloaded and the data may then be analyzed by any suitable method and then provided in the form of a report. The stored data may be accessed wirelessly (e.g., Bluetooth, ZigBee, WiFi (802.11), Wireless USB, ANT or ANT+, Ultrawideband (UWB), IrDA, NFC, etc.) or by wired means (e.g., I2C, USB, Serial, TDMA, etc.). In certain embodiments, a TC2050-IDC (Tag-Connect) or other similar connector can be provided on the ECG monitor to permit serial wire debug and JTAG access to the processing system, including directly connecting to the Flash memory unit of the ECG monitor for downloading data to an external computing device.

The external device used for data analysis may vary. For example, analysis may occur on a smartphone, tablet or PC. Alternatively, analysis may occur a server or other processing device and displayed via a network connection to a remote viewing device. The analysis may also occur using cloud-based distributed processing resources.

Medical information poses significant challenges to knowledge management systems. Medical information includes data that is personal and, while there are legitimate reasons for transmitting medical information files, such transmission must be limited to appropriate circumstances and to authorized recipients. The present devices are designed to prevent the data processing facility from being able to associate a particular device to a particular patient. Specifically, the device is assigned a code, and only the patient's medical practitioner can correlate this code to the patient. The system provides significant protection of protected health information (PHI) while the device is moved by means of the postal or package delivery service, the processing of the device at a location that is not required to observe PHI security protocols, and the return of the ECG test report to the patient's care provider.

Figure 5:
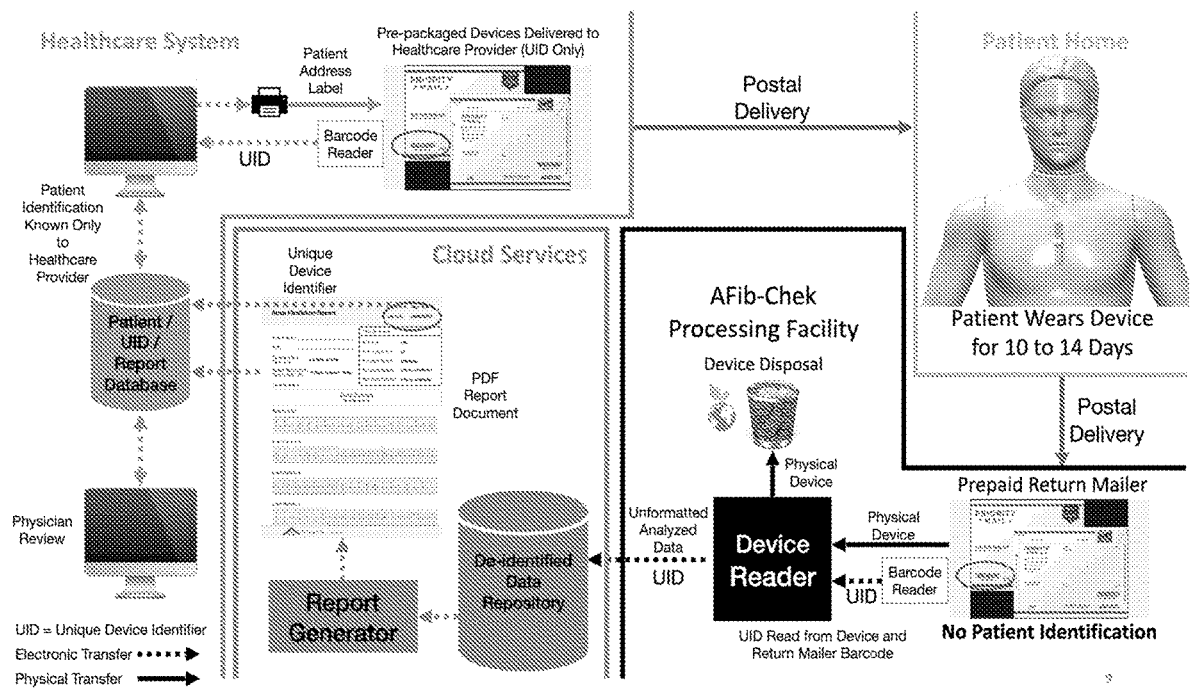
FIG. 5 depicts an example of the system for using the devices of the invention is provided in FIG. 5.

An example of the system for using the devices of the invention is provided in FIG. 5. In practice, the entity responsible for receiving the recorded data from an ECG collection and recording device provides the device to a medical professional. The ECG collection and recording device comprises a unique identifying code stored on a first computer-readable storage medium within the ECG collection and recording device. This unique identifying code is write-protected to prevent unauthorized modification by anyone in the chain of custody of the device, including the medical professional and the patient. The ECG collection and recording device is preferably provided in sealed packaging which is to be mailed to the patient.

The medical professional then associates the ECG collection and recording device to the individual patient by storing the unique identifying code in a record corresponding to the individual in a database file system without removal of the ECG collection and recording device from the sealed packaging. This association between the identifying information and the individual is not provided to the analysis entity. Thus, the entity responsible for receiving the recorded data from an ECG collection and recording device for analysis cannot know the patient's identity.

The medical professional then forwards the ECG collection and recording device to the individual patient in the sealed packaging together with pre-addressed return packaging directing the ECG collection and recording device to the analysis entity. The return packaging provides no identifying information corresponding to the individual to the analysis entity. Rather, the return packaging only contains the unique identifying code stored on a first computer-readable storage medium within the ECG collection and recording device. The individual wears the device, thereby recording ECG data on a computer-readable ECG storage medium within the ECG collection and recording device. Preferably, the packaging is designed so that removal of the ECG collection and recording device from the sealed packaging and/or positioning of the ECG collection and recording device on the individual's body begins the data collection by the device. The computer-readable ECG storage medium may be the first computer-readable storage medium or a second computer-readable storage medium within the device. At the end of the monitoring period, the patient places the ECG collection and recording device in the return packaging and sends the return packaging to the analysis entity.

Upon receipt, the ECG data recorded on the computer-readable ECG storage medium, or a processed form thereof, is stored by the analysis entity on data server in a record corresponding to the unique identifying code. This record may be accessible for reading/viewing by the medical professional, who can associate the data to the individual patient despite there being no identifying information corresponding to the individual stored on the data server. Finally, the analysis entity creates a report of relevant information extracted from the ECG data to the medical professional using the unique identifying code, which the medical professional can associate with the individual patient. This report may be transmitted in any form, including hard copy or as an electronic file. Thus, the association of the device, the report, and the patient identity is known only to the healthcare provider within the provider's HIPPA compliant business environment and relieves the device manufacturer or device processor from the requirement to establish and maintain a HIPPA compliant facility and personnel training and management.

PREFERRED EMBODIMENTS

The following are preferred embodiments of the invention:

1. A body-worn ECG monitor, comprising:
    at least one ECG lead configured be worn on the body of an individual and to measure electrical signals indicative of electrical activity of the individual's cardiac cycle on a continuous basis and generate therefrom an analog waveform;
    sensor electronics comprising an analog-to-digital converter operably connected to the at least one ECG lead to receive the analog waveform or a frequency-filtered form thereof and to generate therefrom a digital waveform;
    a processing component operably connected to the sensor electronics and configured to receive the digital waveform and to continuously monitor the digital waveform for changes in cardiac rhythm indicative of a transient arrhythmic event by
        (i) storing a segment of the digital waveform in a circular data buffer, wherein the stored segment contains digital data for the current cardiac cycle and a plurality of consecutive previous cardiac cycles, and wherein the stored segment is of time length bi and is continuously updated for new cardiac cycles,
        (ii) processing the digital waveform on a beat-by-beat basis to identify an occurrence of a first rhythm transition from a normal cardiac rhythm to an arrhythmia,
        (iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;
        (iv) following the first rhythm transition, processing the digital waveform on a beat-by-beat basis to identify an occurrence of a second rhythm transition from the arrhythmia to a normal cardiac rhythm;
        (v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and
        (vi) repeating steps (ii)-(vi).
2. A body-worn ECG monitor according to embodiment 1, wherein the time lengths $l_2$ and $l_4$ are the same, and the time lengths time lengths $l_3$ and $l_5$ are the same.
3. A body-worn ECG monitor according to embodiment 1 or 2, wherein time lengths $l_2$ and $l_3$ are selected to provide at least about 10 seconds of recorded data that includes the first rhythm transition.
4. A body-worn ECG monitor according to embodiment 3, wherein time lengths $l_2$ and $l_3$ are selected to provide between about 10 and about 240 seconds of recorded data that includes the first rhythm transition.
5. A body-worn ECG monitor according to embodiment 3, wherein time lengths $l_2$ and $l_3$ are selected to provide between about 60 and about 120 seconds of recorded data that includes the first rhythm transition.
6. A body-worn ECG monitor according to one of embodiments 1-5, wherein time lengths $l_4$ and $l_5$ are selected to provide at least about 10 seconds of recorded data that includes the second rhythm transition.

7. A body-worn ECG monitor according to embodiment 6, wherein time lengths $l_4$ and $l_5$ are selected to provide between about 10 and about 240 seconds of recorded data that includes the second rhythm transition.

8. A body-worn ECG monitor according to embodiment 6, wherein time lengths $l_4$ and $l_5$ are selected to provide between about 60 and about 120 seconds of recorded data that includes the second rhythm transition.

9. A body-worn ECG monitor according to one of embodiments 1-8, wherein the circular data buffer holds at least a portion of the digital waveform equal to $l_2$ or $l_4$, whichever is greater.

10. A body-worn ECG monitor according to one of embodiments 1-9, further configured to communicate with an external device to download data stored in the storage memory to a storage medium on the external device.

11. A body-worn ECG monitor according to one of embodiments 1-10, wherein the monitor is a single lead ECG monitor configured to be affixed by means of an adhesive on the chest of the individual at about the level of the heart such that one of the electrodes forming the single lead is positioned superior relative to the other such that the digital waveform approximates a lead II configuration.

12. A body-worn ECG monitor according to embodiment 11, wherein the processing component determines the polarity of the electrodes forming the single lead from the digital waveform data; or wherein the monitor further comprises an accelerometer that is operably connected to the processing component, wherein the processing component is configured to receive one or more accelerometer waveforms from the accelerometer and determine therefrom which electrode in the electrodes forming the single lead is positioned superior relative to the other.

13. A body-worn ECG monitor according one of embodiments 1-12, wherein the first and second rhythm transitions are identified by calculating a randomness score for a series of R-R intervals from the digital waveform using the processing component.

14. A body-worn ECG monitor according to embodiment 13, wherein the randomness score is an entropy value.

15. A body-worn ECG monitor according to embodiment 14, wherein the entropy value is calculated for at least about 128 consecutive QRS complexes in the digital waveform.

16. A system, comprising,
the body-worn ECG monitor according to one of embodiments 1-15; and
the external device, wherein the external device comprises a microprocessor and a non-volatile memory operably connected to the microprocessor, wherein the microprocessor is configured to execute code stored on the non-volatile memory, wherein executing the code causes the external device to display the data downloaded to the storage medium as graphical depictions of ECG waveform segments.

17. A single lead ECG monitor comprising:
a pair of electrodes on the underside of a flexible body coupled to a housing as an integral or unitary device;
electrode traces in the flexible body operably connected the pair of electrodes and to sensor electronics comprising an analog-to-digital converter to receive an analog waveform from the pair of electrodes, or a frequency-filtered form thereof, and to generate therefrom a digital waveform; and
a processing component operably connected to the sensor electronics within the housing and configured to receive the digital waveform and to continuously monitor the digital waveform for changes in cardiac rhythm indicative of a transient arrhythmic event and to store snippets of the digital waveform in a storage memory comprising the changes in cardiac rhythm,
wherein the single lead ECG monitor is configured to be affixed to an individual by means of an adhesive on the flexible body on the chest at about the level of the heart such that one of the electrodes is positioned superior relative to the other such that the digital waveform approximates a lead II configuration.

18. A single lead ECG monitor according to embodiment 17, wherein the processing component determines the polarity of the electrodes forming the single lead from the digital waveform data; or wherein the monitor further comprises an accelerometer that is operably connected to the processing component, wherein the processing component is configured to receive one or more accelerometer waveforms from the accelerometer and determine therefrom which electrode in the electrodes forming the single lead is positioned superior relative to the other.

19. A single lead ECG monitor according to embodiment 17 or 18, wherein the monitor continuously monitors the digital waveform for changes in cardiac rhythm indicative of a transient arrhythmic event by
(i) storing a segment of the digital waveform in a circular data buffer, wherein the stored segment contains digital data for the current cardiac cycle and a plurality of consecutive previous cardiac cycles, and wherein the stored segment is of time length $l_1$ and is continuously updated for new cardiac cycles,
(ii) processing the digital waveform using the processing component on a beat-by-beat basis to identify an occurrence of a first rhythm transition from a normal cardiac rhythm to an arrhythmia,
(iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;
(iv) following the first rhythm transition, processing the digital waveform using the processing component on a beat-by-beat basis to identify an occurrence of a second rhythm transition from the arrhythmia to a normal cardiac rhythm;
(v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and
(vi) repeating steps (ii)-(vi).

20. A method of monitoring a patient, comprising:
affixing a body-worn ECG monitor according to one of embodiments 1-15 to the patient;
recording one or more segments of the digital waveform in the storage memory of the ECG monitor for a period of time;

operably connecting the ECG monitor to an external device comprising a microprocessor and a storage medium; and downloading the one or more segments of the digital waveform to the storage medium.

21. A method according to embodiment 20, wherein the external device further comprises a non-volatile memory operably connected to the microprocessor, wherein the microprocessor is configured to execute code stored on the non-volatile memory, wherein executing the code causes the external device to display the data downloaded to the storage medium as graphical depictions of ECG waveform segments; and executing the code on the microprocessor to display the data.

22. A method of monitoring a patient, comprising:

affixing a single lead ECG monitor according to one of embodiments 17-19 to the patient; and causing the ECG monitor to store snippets of the digital waveform comprising the changes in cardiac rhythm in the storage memory of the ECG monitor for a period of time;

operably connecting the ECG monitor to an external device comprising a microprocessor and a storage medium; and downloading the one or more segments of the digital waveform to the storage medium.

23. A method according to embodiment 22, wherein the external device further comprises a non-volatile memory operably connected to the microprocessor, wherein the microprocessor is configured to execute code stored on the non-volatile memory, wherein executing the code causes the external device to display the data downloaded to the storage medium as graphical depictions of ECG waveform segments; and executing the code on the microprocessor to display the data.

24. A single lead ECG monitor, comprising a pair of electrodes on the underside of a flexible body coupled to a housing as an integral or unitary device;

electrode traces in the flexible body operably connected the pair of electrodes and to sensor electronics comprising an analog-to-digital converter to receive an analog waveform from the pair of electrodes, or a frequency-filtered form thereof, and to generate therefrom a digital ECG waveform; and a processing component operably connected to the sensor electronics within the housing and configured to receive the digital ECG waveform;

wherein the single lead ECG monitor is configured to be affixed to an individual on the chest at about the level of the heart such that one of the electrodes is positioned superior relative to the other on the individual such that the digital ECG waveform approximates a lead II configuration on the individual, wherein the processing component is configured to process the digital ECG waveform and determine therefrom an orientation of the electrodes on the individual such that the single lead ECG monitor is agnostic to the polarity of the digital ECG waveform, and wherein the processing component is further configured to produce ECG data having standard lead II polarity based on the orientation of the electrodes determined by the processing component.

25. A single lead ECG monitor of embodiment 24, wherein the orientation of the electrodes on the individual is determined by the processor:

initially assigning an orientation of the electrodes such that a first electrode of the pair of electrodes is considered to be in a superior position to relative to a second electrode of the pair of electrodes for purposes of producing the ECG data, determining from the digital ECG waveform a polarity metric, and if the polarity metric indicates that the initial orientation assigned to the electrodes was incorrect, assigning a superior position to the second electrode of the pair of electrodes relative to the first electrode of the pair of electrodes for purposes of producing the ECG data.

26. A single lead ECG monitor of embodiment 25, wherein the polarity metric is determined from one or more of (a) a slope of the leading edge of the QRS complex, (b) an amplitude of the largest positive wave, (c) an amplitude of the deepest negative wave, (d) a polarity of the R wave, (e) a polarity of the T-wave, and (f) a polarity of the P-wave.

27. A single lead ECG monitor of one of embodiments 25 or 26, wherein the polarity metric is determined from data in the digital ECG waveform representing a plurality of consecutive cardiac cycles.

28. A single lead ECG monitor of embodiment 27, wherein the polarity metric is determined from data in the digital ECG waveform representing at least 10 consecutive cardiac cycles, wherein at least 70% of the at least 10 consecutive cardiac cycles must agree on the orientation of the electrodes before the polarity metric is used to produce the ECG data.

29. A single lead ECG monitor of one of embodiments 24-28, wherein the orientation of the electrodes is redetermined by the processing component when the processing component determines from the digital ECG waveform that at least one of the pair of electrodes has been repositioned on the individual.

30. A single lead ECG monitor of one of embodiments 24-28, wherein the orientation of the electrodes is redetermined at a predetermined interval during continued use of the ECG data system.

31. A single lead ECG monitor of one of embodiments 26-30, wherein the polarity metric comprises one or more of the following determinations:

if the initial slope of the QRS leading edge is negative and the T-wave is negative, then the polarity metric indicates that the initial orientation assigned to the electrodes was incorrect, if the initial slope of the QRS leading edge is negative and the P-wave is negative, then the polarity metric indicates that the initial orientation assigned to the electrodes was incorrect, if the T-wave is negative and the P-wave is negative, then the polarity metric indicates that the initial orientation assigned to the electrodes was incorrect; or if the amplitude of the largest negative wave is larger than the amplitude of the largest positive wave, then the polarity metric indicates that the initial orientation assigned to the electrodes was incorrect.

32. A single lead ECG monitor according to one of embodiments 24-31, wherein following determination of the orientation of the electrodes by the processing component, the monitor continuously monitors the digital ECG waveform for changes in cardiac rhythm indicative of a transient arrhythmic event by (i) storing a segment of the digital ECG waveform in a circular data buffer, wherein the stored segment contains digital data for the current cardiac cycle and a plurality of consecutive previous cardiac cycles, and wherein the stored segment is of time length $l_1$ and is continuously updated for new cardiac cycles, (ii) processing the digital ECG waveform using the processing component on a beat-by-beat basis to identify an occurrence of a first rhythm transition from a normal cardiac rhythm to an arrhythmia, (iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;

(iv) following the first rhythm transition, processing the digital ECG waveform using the processing component on a beat-by-beat basis to identify an occurrence of a second rhythm transition from the arrhythmia to a normal cardiac rhythm;

(v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and (vi) repeating steps (ii)-(vi).

33. A single lead ECG monitor according to one of embodiments 24-32, wherein the monitor is configured to attach to the individual by means of an adhesive on the flexible body.

34. A method of monitoring a patient, comprising:
affixing a single lead ECG monitor according to one of embodiments 24-33 to the patient;
receiving a digital ECG waveform at the processing component;
executing code on the processing component to determine an orientation of the electrodes on the individual; and
recording ECG data having standard lead II polarity based on the orientation of the electrodes determined by the processing component from the digital waveform in a storage memory of the ECG monitor for a period of time.

35. A method according to embodiment 34, further comprising
operably connecting the ECG monitor to an external device comprising a microprocessor and a storage medium; and
downloading the recorded ECG data to the storage medium.

36. A method according to embodiment 35, wherein the external device further comprises a non-volatile memory operably connected to the microprocessor, wherein the microprocessor is configured to execute code stored on the non-volatile memory, wherein executing the code causes the external device to display the data downloaded to the storage medium as graphical depictions of ECG data; and
executing the code on the microprocessor to display the ECG data.

37. A method for collecting and processing ECG data from an individual, comprising:
providing, by an analysis entity, an ECG collection and recording device to a medical professional, wherein the ECG collection and recording device comprises a unique identifying code stored on a first computer-readable storage medium within the ECG collection and recording device, wherein the unique identifying code is write-protected to prevent unauthorized modification thereto, and wherein the ECG collection and recording device is provided in sealed packaging;

associating, by the medical professional, the ECG collection and recording device to the individual by storing the unique identifying code in a record corresponding to the individual in a database file system without removal of the ECG collection and recording device from the sealed packaging, wherein identifying information corresponding to the individual is not provided to the analysis entity;

providing, by the medical professional, the ECG collection and recording device to the individual in the sealed packaging together with return packaging for return of the ECG collection and recording device to the analysis entity following use of the ECG collection and recording device by the individual, wherein the return packaging provides no identifying information corresponding to the individual to the analysis entity;

recording, by the individual, of ECG data on a computer-readable ECG storage medium within the ECG collection and recording device by removal of the ECG collection and recording device from the sealed packaging and operably connecting the ECG collection and recording device to the individual's body for a period of time, wherein the computer-readable ECG storage medium may be the first computer-readable storage medium or a second computer-readable storage medium;

providing, by the individual, the ECG collection and recording device to the analysis entity by placing the ECG collection and recording device in the return packaging and transferring the return packaging to the analysis entity;

reading, by the analysis entity, the ECG data recorded on the computer-readable ECG storage medium, wherein the ECG data, or a processed form thereof, is stored by the analysis entity on data server in a record corresponding to the unique identifying code that is accessible for reading by the medical professional, wherein no identifying information corresponding to the individual is stored on the data server; and electronically transmitting, by the analysis entity to the medical professional, an analysis report derived from the ECG data, wherein the analysis entity associates the analysis report with the unique identifying code such that the medical professional can associate the analysis report with the individual.

38. The method of embodiment 37, wherein the ECG collection and recording device is a body-worn ECG monitor according to one of embodiments 1-15 or a single lead ECG monitor according to one of embodiments 17-19 or 24-33.

39. A body-worn ECG monitor according to one of embodiments 1-15, wherein the body-worn ECG monitor is a single lead ECG monitor according to one of embodiments 17-19 or 24-33.

40. A method according to one of embodiments 20 or 21, wherein the body-worn ECG monitor is a single lead ECG monitor is a single lead ECG monitor according to one of embodiments 17-19 or 24-33.

41. A method according to one of embodiments 34-36, wherein the single lead ECG monitor is a body-worn ECG monitor according to one of embodiments 1-15.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patent applications, patents, publications and other references mentioned in the specification are indicative of the levels of those of ordinary skill in the art to which the invention pertains and are each incorporated herein by reference. The references cited herein are not admitted to be prior art to the claimed invention.

Unless otherwise defined, all technical and scientific terms used herein have the same meaning as commonly understood by one of ordinary skill in the art to which this invention belongs. In the case of conflict, the present specification, including definitions, will control.

The use of the articles "a", "an", and "the" in both the description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally, whenever "comprising" or another open-ended term is used in an embodiment, it is to be understood that the same embodiment can be more narrowly claimed using the intermediate term "consisting essentially of" or the closed term "consisting of".

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 10% more or less than the specified value. In another embodiment, the term "about" refers to a range of values which are 5% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the terms "between X and Y" and "range from X to Y, are inclusive of X and Y and the integers there between. On the other hand, when a series of individual values are referred to in the disclosure, any range including any of the two individual values as the two end points is also conceived in this disclosure.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

I claim:

1. A body-worn ECG monitor, comprising:
at least one ECG lead configured be worn on the body of an individual and to measure electrical signals indicative of electrical activity of the individual's cardiac cycle on a continuous basis and generate therefrom an analog waveform;
sensor electronics comprising an analog-to-digital converter operably connected to the at least one ECG lead to receive the analog waveform or a frequency-filtered form thereof and to generate therefrom a digital waveform;
a processing component operably connected to the sensor electronics and configured to receive the digital waveform and to continuously monitor the digital waveform for changes in cardiac rhythm indicative of a transient arrhythmic event by
(i) storing a segment of the digital waveform in a circular data buffer, wherein the stored segment contains digital data for the current cardiac cycle and a plurality of consecutive previous cardiac cycles, and wherein the stored segment is of time length $b_i$ and is continuously updated for new cardiac cycles,
(ii) processing the digital waveform on a beat-by-beat basis to identify an occurrence of a first rhythm transition from a normal cardiac rhythm to an arrhythmia,
(iii) upon identifying the first rhythm transition, initiating storage of data from the data buffer into a storage memory beginning from a point in the data preceding the first rhythm transition by a predetermined time length $l_2$, and ending the storage of data at a predetermined time length $l_3$ following the first rhythm transition;

(iv) following the first rhythm transition, processing the digital waveform on a beat-by-beat basis to identify an occurrence of a second rhythm transition from the arrhythmia to a normal cardiac rhythm;

(v) upon identifying the second rhythm transition, initiating storage of data from the data buffer into a storage memory beginning from a point in the data preceding the second rhythm transition by a predetermined time length $l_4$ and ending the storage of data at a predetermined time length $l_5$ following the second rhythm transition; and (vi) repeating steps (ii)-(vi).

2. A body-worn ECG monitor according to claim 1, wherein the time lengths $l_2$ and $l_4$ are the same, and the time lengths time lengths $l_3$ and $l_5$ are the same.

3. A body-worn ECG monitor according to claim 2, wherein time lengths $l_2$ and $l_3$ are selected to provide at least about 10 seconds of recorded data that includes the first rhythm transition.

4. A body-worn ECG monitor according to claim 3, wherein time lengths $l_2$ and $l_3$ are selected to provide between about 10 and about 240 seconds of recorded data that includes the first rhythm transition.

5. A body-worn ECG monitor according to claim 3, wherein time lengths $l_2$ and $l_3$ are selected to provide between about 60 and about 120 seconds of recorded data that includes the first rhythm transition.

6. A body-worn ECG monitor according to claim 1, wherein time lengths $l_4$ and $l_5$ are selected to provide at least about 10 seconds of recorded data that includes the second rhythm transition.

7. A body-worn ECG monitor according to claim 6, wherein time lengths $l_4$ and $l_5$ are selected to provide between about 10 and about 240 seconds of recorded data that includes the second rhythm transition.

8. A body-worn ECG monitor according to claim 6, wherein time lengths $l_4$ and $l_5$ are selected to provide between about 60 and about 120 seconds of recorded data that includes the second rhythm transition.

9. A body-worn ECG monitor according to claim 1, wherein the circular data buffer holds at least a portion of the digital waveform equal to $l_2$ or $l_4$, whichever is greater.

10. A body-worn ECG monitor according to claim 1, further configured to communicate with an external device to download data stored in the storage memory to a storage medium on the external device.

11. A body-worn ECG monitor according to claim 1, wherein the monitor is a single lead ECG monitor configured to be affixed by means of an adhesive on the chest of the individual at about the level of the heart such that one of the electrodes forming the single lead is positioned superior relative to the other such that the digital waveform approximates a lead II configuration.

12. A body-worn ECG monitor according to claim 11, wherein the processing component determines the polarity of the electrodes forming the single lead from the digital waveform data; or wherein the monitor further comprises an accelerometer that is operably connected to the processing component, wherein the processing component is configured to receive one or more accelerometer waveforms from the accelerometer and determine therefrom which electrode in the electrodes forming the single lead is positioned superior relative to the other.

13. A body-worn ECG monitor according claim 1, wherein the first and second rhythm transitions are identified by calculating a randomness score for a series of R-R intervals from the digital waveform using the processing component.

14. A body-worn ECG monitor according to claim 13, wherein the randomness score is an entropy value.

15. A body-worn ECG monitor according to claim 14, wherein the entropy value is calculated for at least about 128 consecutive QRS complexes in the digital waveform.

16. A method of monitoring a patient, comprising:

affixing a body-worn ECG monitor according to claim 1 to the patient;

recording one or more segments of the digital waveform in the storage memory of the ECG monitor for a period of time;

operably connecting the ECG monitor to an external device comprising a microprocessor and a storage medium; and downloading the one or more segments of the digital waveform to the storage medium.

* * * * *